United States Patent [19]

Strauss

[11] Patent Number: 5,755,788
[45] Date of Patent: May 26, 1998

[54] PROSTHESIS AND IMPLANTS HAVING LIPOSOMES BOUND THERETO AND METHODS OF PREPARATION

[75] Inventor: George Strauss, Piscataway, N.J.

[73] Assignee: Rutgers, The State University, New Brunswick, N.J.

[21] Appl. No.: 640,407

[22] Filed: Apr. 30, 1996

Related U.S. Application Data

[63] Continuation of Ser. No. 982,160, Nov. 25, 1992, abandoned, which is a continuation of Ser. No. 396,788, Feb. 21, 1989, abandoned, which is a continuation of Ser. No. 17,185, Feb. 19, 1987, abandoned.

[51] Int. Cl.$^6$ .............................. A61F 2/02; A61F 2/24; A61F 2/16; A61F 2/28
[52] U.S. Cl. .................................. 623/11; 623/6; 623/2; 623/3; 623/16; 623/1
[58] Field of Search .................... 623/1, 2, 11, 12, 623/66, 6, 3, 16

[56] References Cited

U.S. PATENT DOCUMENTS

| | | | |
|---|---|---|---|
| 4,348,329 | 9/1982 | Chapman | 623/1 |
| 4,442,133 | 4/1984 | Greco et al. | 623/1 |
| 4,612,370 | 9/1986 | Hunt | 536/5 |
| 4,671,410 | 6/1987 | Hansson et al. | 206/438 |
| 4,749,585 | 6/1988 | Greco et al. | 623/12 |
| 4,880,635 | 11/1989 | Janoff et al. | |
| 4,883,665 | 11/1989 | Miyzzima et al. | 424/417 |
| 4,963,362 | 10/1990 | Rahman et al. | 424/450 |
| 5,206,347 | 4/1993 | Ruoslahti et al. | 530/413 |

OTHER PUBLICATIONS

Harvey, et al., Abstract, "Vascular Protheses With Reduced Thrombogenicity", Federation of American Societies for Experimental Biology, Apr. 21–26, 1985.

Harvey, et al., The Binding Of Encapsulated Drugs to the Surface of Protheses, International Symposium on Artificial Organs, Biomedical Engineering & Transplantation, Jan. 20–23, 1986.

Hauser, et al., "Stabilization of Small Unilamellar Phospholipid Vesicles During Spray–Drying", Biochemica et Biophysica Acta 897, pp. 331–334, (1987).

Strauss, et al., "The Interaction of Saccharides With Lipid Bilayer Vesicles: Stabilization During Freeze–Thawing and Freeze–Drying", Biochimica et Biophysica Acta 858, pp. 169–180, (1986).

Strauss, et al., "Stabilization of Lipid Bilayer Vesicles by Sucrose During Freezing", Proc. Natl. Acad. Sci. USA, vol. 83, pp. 2422–2426, Apr., 1986.

Yao et al., "Adsorption of Quaternary Ammonium Surfactants on Poly(tetrafluoroethylene) Surfaces", American Chemical Society, pp. 2353–2357, (1991).

Yao et al., "Adsorption of Cationic Surfactants on Medical Polymers: Effects of Surfactant and Substrate Structures", American Chemical Society, pp. 2274–2278, (1992).

*Primary Examiner*—Debra S. Brittingham
*Attorney, Agent, or Firm*—Mathews, Collins, Shepherd & Gould, P.A.

[57] ABSTRACT

Prostheses and implants are provided which have bound liposomes which are freeze-thaw and dehydration stable and which resist infection and thrombosis development in the body. Stabilizing agents are used, including saccharide stabilizing agents. Prosthesis and implant kits are provided which have long shelf stability. Processes for making the prostheses and implants of the invention and for preparing the prostheses and implants for liposome binding are provided.

22 Claims, No Drawings

PROSTHESIS AND IMPLANTS HAVING LIPOSOMES BOUND THERETO AND METHODS OF PREPARATION

This application is a continuation of application Ser. No. 07/982,160, filed Nov. 25, 1992, now abandoned, which is a continuation of application Ser. No. 07/396,788, filed Feb. 21, 1989, now abandoned, which is a continuation of application Ser. No. 07/017,185, filed Feb. 19, 1987, now abandoned.

TECHNICAL FIELD

This invention relates to prostheses and implants used in in vivo surgery, which have bound thereto liposomes in which one or more pharmaceuticals are enveloped. The liposomes can be bound to the prostheses or implants by treating the surfaces first with an amphiphilic agent or by using liposomes having available functional groups which result in binding to those surfaces. The liposomes can be reacted with effective amounts of saccharides or other saccharide stabilizing agents which render the liposomes stable to freezing and thawing or dehydration, which liposomes, if dehydrated, are capable of rehydration. The invention also relates to methods of preparation of the prostheses and implants provided by the invention and to certain liposomes.

BACKGROUND ART

Various prostheses or implants are used to replace damaged or malfunctioning portions of the body or to supplement the functioning of a body organ or other body portion. For example, it is common to replace damaged or partially clogged blood vessels. Certain joints are replaced with metal or polymeric joints, such as hip and knee joints. Implants are placed into the body by in vivo surgery to supplement or replace the functioning of an organ of the body, such as a pacemaker, a drug diffusion pump, and the like.

In the past, notwithstanding the care and quality exercised in surgery, there have been substantial incidences of infection and thrombosis as a consequence of the surgical placement of a prosthesis or implant into a body. Often the prosthesis or implant must be removed or bypassed or some other drastic measure must be applied to cope with such problems. This presents a very serious consideration and answers to prevent or greatly diminish such problems in use of prostheses and implants are highly desired.

In the past, prostheses or implants such as those made of metallic substances, polytetrafluoroethylene or poly (ethylene-p-phthalate) have been treated with an amphiphilic agent such as the cationic surfactant TDMAC (tridodecylmethyl ammonium chloride) dissolved in a solvent such as ethanol and have subsequently been treated with an anionic antibiotic such as penicillin, which will bind to such amphiphilic agent previously bound to the surfaces. Such anionic antibiotics have carboxylic acid groups, which can be reacted with the cationic groups of a surfactant such as TDMAC. It also has been disclosed that another surfactant, benzalkonium chloride, has been used to treat prosthesis surfaces. However, it has been shown that greater absorption and more effectiveness has been attained by the use of TDMAC.

One of the problems in utilization of prostheses and implants following this previous procedure is that it is usually required to carry out many or all of the steps in the actual operating room. Another difficulty with utilization of this previous technology is that the pharmaceutical must be selected which will bind with the functional pendant groups of the amphiphilic agent which has been used in treating the surfaces of the prostheses or implants. This can substantially limit the character of antibiotics or other pharmaceuticals which can be utilized. Often, it might be desired to use combinations of pharmaceuticals wherein one of the pharmaceuticals is cationic or anionic and the other one has the opposite ionic character or perhaps it might be non-ionic. It was difficult, if not impossible, to utilize such pharmaceutical selections in this previous system. Also, it has been found that if the prostheses or implants are prepared by first treating the surfaces thereof with a surfactant such as TDMAC and then treated so as to bind the pendant cationic groups of the surfactant with anionic groups of a pharmaceutical, there can be an excess of surfactant molecules bound on the prostheses or implant surfaces which have not reacted with anionic groups of the pharmceutical. It is believed that these groups can contribute to formation of thrombosis within the body in the environment of the prosthesis or implant present in the body.

It is desired to utilize liposomes to deposit certain pharmaceuticals on the surfaces of prostheses or implants. One problem with the use of liposomes has been the complication of preparing fresh liposomes in the operating room. This can present considerable difficulties and risk since the timing correlation of liposomes preparation with the surgical steps can be difficult and the liposome preparation in the operating room is not within the normal practices of the surgeon or his attendants. Also, the preparation of prostheses or implants utilizing liposomes can take considerable time.

It is therefore desired to have improved prostheses and implants which have bound thereto liposomes and which resist infections or thrombosis formation in the environment of the prostheses or implants when they are embedded into the body by in vivo surgery. It would further be desired that the liposomes which are bound to the surfaces of the prostheses or implants be resistant to degradation upon freezing and thawing or dehydration. This will permit the prostheses or implants to be made outside the operating room and to be made available to the surgical staff in the operating room in a sterile preformed condition or as a sterile kit. It is desired that the quantity of surfactant or other amphiphilic agent which is not bound to the liposomes, if such amphiphilic agent is used, will be of sufficiently low quantity so as to preclude any substantial tendency to cause thrombosis. It further would be highly desirable to have prostheses and implants which do not utilize amphiphilic agents as a separate and distinct treatment on the surfaces of the prostheses or implants and to have prostheses and implants having bound to the surfaces thereof liposomes carrying one or more pharmaceuticals in which the liposome is provided in frozen or dehydrated form, either by lypholization, spray drying or other means of dehydration and which liposomes can be readily rehydrated.

SUMMARY OF INVENTION

This invention relates to an improved prosthesis or implant for use in in vivo surgery which utilizes liposomes with an ionic charge opposite to the charge on the surface of the prosthesis or implant. It is desired and is provided by this invention prostheses and implants in which liposomes are utilized, which liposomes envelop one or more pharmaceuticals which are bound to the surfaces of the prostheses or implants without having an excess or substantially excessive amounts of surfactants or other agents broadly referred to as amphiphilic agents, but rather having a minimal amount of such unbound amphiphilic agents. Such freedom from unbound amphiphilic agents is believed to reduce the possibility for development of thrombosis.

This minimal content of amphiphilic agent on the surface of the prostheses or implants can be provided by treating the surface thereof with a selected dilute solution of the amphiphilic agent for a time in order to maintain a desired minimal content of amphiphilic agent on the surfaces of the prostheses or implants. Also, the superfluous quantity of amphiphilic agent molecules on the surfaces of the prostheses or implants can be removed prior to treatment with the liposomes bearing the pharmaceutical or pharmaceuticals with an agent that will scrub or remove all or at least the excessive amount on the outer surfaces of the prostheses or implants. Sometimes it is desirable to remove the amphiphilic agents on the outer surfaces and leave the amphiphilic agent molecules bound within the pores or crevices of the surfaces of the prostheses and implants. This will vary depending upon the prosthesis or implant and the particular liposome bearing a pharmaceutical or pharmaceuticals.

Also provided by this invention are prostheses and implants which have bound thereto liposomes which envelop one or more pharmaceuticals and which are made using not only the usual phospholipid or other liposome-forming compound, optionally also other agents, one or more of which have groups which will bind directly to the surfaces of the prostheses or implants. By this means, it is possible to preclude the use or the presence of excessive amphiphilic agent.

Use of the above described prostheses or implants permits preparation of them outside of the operating room. The prosthesis or implant then is frozen or dehydrated, causing the bound liposomes to be frozen or dehydrated. The frozen prosthesis or implant can be dehydrated by placing it in vacuum until the water is removed by lypholization. The prosthesis or implant then can be readied in the operating room for use in in vivo surgery by rehydration or warming, as the case may be, causing reconstitution of the bound liposomes. Such prostheses or implants can be provided wherein the bound liposomes are stabilized, for example, by use of one or more saccharide stabilizing agent, such as mono- or di-saccharides or glycosides thereof which have a lipophilic moiety, such as one or more long chain alkyl groups.

This invention is also directed to processes for preparation of certain of the prostheses and implants which are the subject of this invention and also is directed to certain of the liposomes themselves which are capable of binding to the surfaces of the prostheses or implants without utilization of an amphiphilic agent.

DETAILED DESCRIPTION OF THE INVENTION AND THE PREFERRED EMBODIMENTS

A wide variety of prostheses or implants can be used to illustrate the invention. For example, polytetrafluoroethylene prostheses can be used. Suitable polytetrafluoroethylene prostheses can be made from a porous product sold under the designation Gore-Tex. Other suitable materials can be used in order to form prostheses, as is within the skill of the art. For example, certain polyester materials such as poly(ethylene-p-phthalate) materials can be used as well as certain other polymers. The selection depends upon the particular use, the amount of load-bearing required of the prostheses, and other considerations. Also, metal prostheses can be used. For example, certain alloys can be utilized in forming prostheses in suitable form. Suitable metallic substances can be selected from the following: stainless steel, titanium, cobalt-chromium alloy, microstructured titanium and cobalt-chromium alloys, and other suitable metallic materials which are suitable for use in construction of prostheses or implants and which provide surfaces which permit binding of liposomes.

Suitable polymeric materials for making the protheses and implants can be selected from the following: polyfluoroethylenes, such as polytetrafluoroethylenes; polytrifluoroethylenes and polytrifluorochloroethylenes; polyurethanes; polyesters, such as poly(ethylene-p-phthalate); polyethylenes; polypropylenes; polyvinylchlorides; polyamides; polyacrylamides; polycarbonates; polyoxymethylenes and copolymers having oxymethylene groups; polyglycolic acid; polylactic acid; polyacrylics such as polymethacrylates and polyacrylates; elastomers such as polysiloxane polymers, and the like.

The type of prostheses can vary substantially within the scope of this invention. For example, vascular prostheses can be utilized within this invention. Other prostheses include the following types: heart valves, orthopedic prostheses such as hip and knee replacements, ventricular and peritoneovenous shunts, penile prostheses, intraocular prostheses, catheters of various types, and others.

Various implants can be utilized in practicing the invention. For example, pacemakers, certain diffusion pumps such as used in delivering various pharmaceuticals, such as insulin and the like.

The selected prostheses can suitably be treated with a selected amphiphilic agent. The amphiphilic agent can be a surfactant, either anionic or cationic surfactant, or it can be another compound which when exposed to the surfaces of the prosthesis or implant will suitably bind to the surfaces. Such binding can provide sites which can react or otherwise bind with the liposomes used in this invention. The particular amphiphilic agent will be selected depending upon the character of the prosthesis, the environment in which it is used, the charge desired (anionic or cationic) and other considerations. It has been found that frequently a cationic surfactant such as tridodecylmethyl ammonium chloride (TDMAC) can be used. A cationic surfactant can be utilized if the liposomes have generally a negative charge (are anionic) which will result in binding of the liposomes to the surface as desired. Alternatively, an anionic amphiphilic agent, such as phosphitidyl serine, can be applied to the prosthesis, followed by application of liposomes made using phospholipids or other compounds having cationic groups. Anionic amphiphilic agents can be selected from surfactants which will bind to the prosthesis or implant and which will then further bind to positively charged liposomes as described herein. Such anionic surfactants can be selected from the general classes of carboxylic acids, sulfonates, sulfates, sulfonates and the like. Cationic amphiphilic agents can also be selected from surfactants which will bind to the prosthesis or implant and which will then further bind to negatively charged liposomes as described herein. Such cationic surfactants can be selected from the general classes of quaternary ammonium salt compounds, amines, derivatives thereof, and the like. Anionic and cationic amphiphilic agents can be used which are outside the scope of surfactants. The amphiphilic agents selected will be biocompatible and compatible with the prostheses or implants and with the liposomes to be bound hereto. The prostheses or implants themselves can have positive or negative charges on their surfaces which will bind the liposomes of opposite charge. For examples, the prosthesis or implant can be made of a polymer having an amount of carboxylic acid or quaternary ammonium salt groups or have a surface coating of such polymer, which will bind liposomes as provided herein on the surfaces thereof.

The amphiphilic agent can be dissolved in a suitable solvent which is acceptable to the prosthesis or implant utilized in carrying out the invention. A suitable solvent is, generally speaking, an organic solvent which is compatible with and can be easily removed from the final prosthesis or implant. Such solvents include methanol, ethanol, isopropyl alcohol, and others which are compatible and suitable for use. It has been found that a minimal amount of the surfactant on the prosthesis or implant surfaces which will effectively bind the desired amount of liposomes, is preferable. Substantial excess of the amphiphilic agent can contribute, it is believed, to incompatibility of the prosthesis or implant with the surrounding environment and to reduced stability and binding of the liposomes. For example, it is presently believed that a substantial excess of the amphiphilic agent groups, can contribute to the mechanisms by which thrombosis results.

Therefore, it is desirable to follow a procedure by which substantial excess of the amphiphilic agent derived groups is avoided. For example, the concentration of the amphiphilic agent can be used at relatively dilute concentrations, such as 1 percent or less to as low as 0.1 percent or lower, depending upon the solvent, the amphiphilic agent and other factors. If a surfactant such as TDMAC is used, a suitable solvent is methanol and a concentration of 0.1 to 1 percent of TDMAC is suitable. It has been found that a concentration of amphiphilic compound in the range of about 0.2 to about 0.8 percent by weight is usually more desirable, with a concentration of about 0.5 percent being a presently preferred concentration. It is believed that the exposure time of this amphiphile-solvent combination can be limited in order to prevent an excessive amount of amphiphilic agent being bound on the prosthesis or implant surfaces. It has been found that a 0.5 percent concentration of TDMAC in methyl alcohol will provide adequate amphiphilic groups on a prosthesis or implant, such as those made of polytetrafluoroethylene, such as sold under the designation Gore-Tex, if the treatment time is about 1 hour. To determine a proper amount of amphiphilic agent to be bound to a prosthesis surface, a series of test prosthesis parts can be treated with increasing amounts of amphiphilic agent. A given amount of liposomes are bound to those prosthesis parts. A plot of the binding of liposomes versus amount of amphiphilic agent will show the minimal point at which the liposomes are bound.

Another means by which to reduce the excess is to treat the surfaces of the prostheses or the implants with a material, usually in a solid particulate form, which is capable of reducing the amount of the amphiphilic agent bound to the surface of the prosthesis or implant. If the amphiphilic compound is cationic, such as provided by treatment with TDMAC, a suitable material for removing the excess, particularly on the outer surfaces of the prosthesis or implant, is to treat the surface with an aqueous suspension of gel particles, such as sold under the designation CM-Sepharose, which is a cross-linked carboxymethyl agarose cation exchange resin available commercially. If the bound amphiphilic agent is anionic, a suitable aqueous suspension of gel particles can be used effectively, such as sold under the designation DEAE-Sepharose, a cross-linked agarose anion exchange resin. Other materials can be used and will be suggested to those skilled in the art, depending on the nature of the amphiphilic agent utilized, the compatibility of such material with the process for making the prosthesis or implant products of this invention and the overall compatibility of the materials with the final biological purpose.

Often it is desired to remove bound amphiphilic agent molecules from the surface of the prosthesis or implant and have the amphiphilic agent remain on the surfaces of the pores or crevices of the prosthesis or implant. In this event, a particle size used for the amphiphile removal agent will preferably be selected which is larger than the openings to the pores or crevices so as to leave the bound amphiphilic agent compound on the surfaces of the pores and crevices.

The liposomes as used by this invention encapsulate certain pharmaceuticals which it is desired to have present on the surfaces of the prostheses or implants. Ordinarily, such materials are utilized for the purposes of preventing or diminishing the development of infection on the surfaces or in the environment of the prosthesis or implant placed into the body by surgery. Other pharmaceuticals can be utilized, depending upon the desire for such materials on the prosthesis or implant. Such materials include substances which have an anti-thrombogenicity activity, materials which will promote the compatibility of the implant or prosthesis with the body or environment of the body, and the like. An antibiotic, if utilized, can vary substantially so long as the antibiotic can be enveloped in the liposomes, is biocompatible and effective. The antibiotic can be water soluble and then will be dissolved in the aqueous solution used to make the aqueous phase of the liposomes. If the antibiotic is slightly soluble or insoluble in water, it can be incorporated into the lipid used in making the liposomes. The antibiotic can be selected from a variety of penicillins, including a variety of the many biosynthetic penicillins available. Other antibiotics can be used as desired and as suitable for use in the particular prosthesis or implant. Such antibiotics can be selected from tetracycline-type antibiotics, cephalosporins, erythromycin and its derivatives, chloroamphenicol, griseofulvin, gentamycin, kanamycin, novobrocin, polymyxin, refampin, streptomycin, lincomycin, and the like.

Anti-thrombotic pharmaceuticals can be used. Such a pharmaceutical can be selected from acetylsalicylic acid, dipyridamole, heparin, ibuprofen, indomethacin, prostaglandins, sulfinpyrazone, warfarin, and the like.

Thrombolytic enzymes can be used in making the liposomes. Such pharmaceuticals can be selected from streptokinase, urokinase, plasminogen activator, and the like.

Combinations of pharmaceuticals can be used in making the liposomes. For example, combinations of antibiotics or of antibiotics with other pharmaceuticals can be included in the liposomes or a combination of liposomes, some of which have antibiotic and some of which have other desired pharmaceutical properties.

The liposomes can be made by dissolving a liposome-forming compound or combination of such compounds in a suitable solvent. For example, lecithin (phosphatidylcholine), phosphatidylserine, or other suitable natural or synthetic phospholipids can be dissolved in a solvent such as chloroform or the like. Phospholipids suitable for making liposomes either alone or in combination can be selected from the following: Egg phosphatidylcholine (EPC); Dilauryloylphosphatidylcholine (DLPC); Dimyristoylphosphatidylcholine (DMPC); Dipalmitoylphosphatidylcholine (DPPC); Distearoylphosphatidylcholine (DSPC); 1-Myristoyl-2-palmitoylphosphatidylcholine (MPPC); 1-Palmitoyl-2-myristoyl phosphatidylcholine (PMPC);

1-Palmitoyl2-stearoyl phosphatidylcholine (PSPC); 1-Searoyl-2-palmitoyl phosphatidylcholine (SPPC); Diooleoylphosphatidylcholine (DOPC); Dilauryloylphosphatidylglycerol (DLPG); Dimyristoylphosphatidylglycerol (DMPG); Distearoylphosphatidylglycerol (DSPG); Dioleoylphosphatidylglycerol (DOPG); Dimyristoyl phosphatidic acid (DMPA); Dipalmitoyl phosphatidic acid (DPPA); Dipalmitoyl phosphatidic acid (DPPA); Dimyristoyl phosphatidylethanolamine (EMPE) Dipalmitoyl phosphatidylethanolamine (DPPE); Dimyristoyl phosphatidylserine (DMPS); Dipalmitoyl phosphatidylserine (DPPS); Brain phosphatidylserine (PS); Brainsphingomyelin (BSP); Dipalmitoyl sphingomyelin (DPSP); Distearoyl sphingomyelin; and the like. Certain amphiphilic compounds such as TDMAC, dihexadecyldimethyl ammonium bromide and the like can be used.

An amount of a stiffening agent can be incorporated into the liposome-forming mixture such as a suitable steroid, for example, cholesterol, ergo-sterol, coprostanol, cholestanol, cholestane and the like. Cholesterol has been suitable for such use, such as about 1 to about 40 percent, based on the weight of liposome-forming mixture.

A suitable amount of the phospholipid or other liposome-forming compound is dissolved in such solvent and the solution is placed into a suitable reaction vessel, such as a round bottom flask. The flask or other reactor is rotated under vacuum so that the phospholipid or other compound is deposited as a thin film on the inner wall of the flask. The antibiotic or other pharmaceutical is then dissolved in an aqueous solution, such as a buffered aqueous solution. The aqueous solution is selected so as to maintain the pharmaceutical in a desired state. A solution of the antibiotic or other pharmaceutical is added to the flask and it is agitated using, for example, a vortex mixer, whereby there is a dispersion of the antibiotic or other pharmaceutical aqueous mixture and the phospholipid used to form the liposomes. The mixture is then subjected to sonication with a suitable sonicator. The mixture is generally initially turbid but becomes relatively clear when sonication results in liposome formation.

The sonicator may be a probe-type or it may be a bath type. Frequently, it is advantageous to use a bath type if it is desired that the solvent or other contents of the reaction mixture not escape into the atmosphere.

If a phospholipid is employed, a suitable amount of the phospholipid liposome-forming material can be about one part of phospholipid to about one part of the antibiotic or other pharmaceutical. Larger amounts of the liposomes can be made using appropriate scale-ups. The sonication can be carried out using appropriate wattage, such as from about 5 watts to 50 watts, when a probe-type sonicator is used. The sonication is continued until small liposomes are formed, at which point the initially turbid liquid becomes almost clear. The length of time for carrying out this reaction varies with the intensity of the sonication and other factors. Normally the reaction requires a substantial period of time such as from about 30 to 60 minutes or more. Normally, the sonication can be carried out at generally ambient temperatures or another temperature which is somewhat lower or higher without substantially interfering with the formation of the liposomes, provided that the temperature used is above the transition temperature of the lipid employed.

The liposomes desirably are of a moderate size and desirably are of a unilamellar configuration. However, at times it is desirable to have a multilamellar configuration. Generally speaking, it is preferred to use liposomes having a small size, less than 100 nanometers in diameter, desirably about 25 to about 75 nanometers in diameter. However, the size can be increased or decreased somewhat and still be effective and at times such smaller or larger liposomes can be desirable or preferable.

Liposomes having a size under 100 nanometers are considered in the art to be small unilamellar liposomes. On the other hand, liposomes having a size greater than 100 nanometers are considered to be large (large unilamellar liposomes).

Multilamellar liposomes can be made as by using vortexing alone or by using a reduced degree of sonication. There are also other methods known to the art.

It has been found preferable to utilize in this invention liposomes which have been stabilized against damage by freezing or drying. It has been found that these liposomes so stabilized can be applied to the prosthesis or implant outside the operating room under conditions which foster careful quality control and production methods. If properly stabilized, the liposomes can be frozen or freeze-dried or otherwise dried and can be stored indefinitely under sterile conditions. Prostheses or implants with such liposomes and so produced are highly desirable from many points of view. The bound liposomes of these prostheses or implants can be rehydrated or warmed and brought back to original stable condition, which are viable when inserted into the body by surgery. Such produced prostheses or implants which are frozen or dehydrated can be appropriately placed into a package, such as a sealed plastic pouch, and appropriately sterilized to provide a sterile kit which can be brought into the operating room for implantation or insertion by surgery into the body. Suitable polymers can be used to make the heat sealed kits, such as polyvinylchloride, polyester, certain coextruded films, and the like. This obviously provides a highly convenient form and permits a very substantial reduction in risk in utilizing prostheses or implants having bound liposomes.

It has been found that a variety of materials can be utilized to bring about the stabilization. It has been found, for example, that certain saccharide stabilizing agents, such as mono- and di-saccharides, can be used. It has been found, for example, that sucrose, trehalose, glucose, and glycosides of saccharides, such as those which have a lipophile moiety with one or more long chain alkyl groups, are satisfactory. Stabilization can provide against disruption of the liposomes by freezing and thawing or dehydration by utilizing a saccharide stabilizing agent, such as sucrose or trehalose, into an aqueous solution in which the pharmaceutical is dissolved. A concentration of about 1 to about 10 percent of sucrose or trehalose has been found suitable. Also, it has been found that stabilization can occur by exposing the formed liposomes to a solution such as an aqueous solution containing the saccharide stabilizing agent. For example, sucrose or trehalose can be dissolved in an aqueous solution and exposed to the surfaces of the formed liposomes. The amount of sucrose or trehalose or other stabilizing agent is used in molar quantities exceeding the molar amount of the phospholipid or other compound utilized in making the liposomes. The aqueous solution containing the stabilizing agent as well as the formed liposomes can suitably be used to contact the prosthesis or implant for binding the liposomes thereto.

The drying or freeze-drying is preferably carried out while the liposomes are surrounded by such stabilizing aqueous solution. For example, the liposomes can be suspended in a solution containing 1 to 10 percent sucrose or trehalose. It is not desired to be bound by any particular scientific theory as to the reason the liposomes as present on the prostheses or implants are stable to such dehydration and rehydration or freezing or freeze-drying. However, it is felt that one possible explanation is that the stabilizing agent complexes with the liposome-forming compounds, thereby stabilizing the liposome structure.

The prostheses or implants can be evaluated as to the effectiveness of the binding of liposomes which carry the desired pharmaceutical. This can be carried out by utilizing, for example, polytetrafluoroethylene specimens. The tests are illustratively conducted as follows.

Tests for Adherence of Liposones and of Amphiphilic Antibiotics to Prostheses

To 20 mg phosphatidylserine (PS) or other lipid, 0.1 mg of dioctadecyloxacarbocyanine (DCY) is added, which is a fluorescent dye. The lipid and dye are dissolved in chloroform/methanol combination, and evaporated to dryness. Liposomes are prepared as described in Example 1. This fluorescent dye becomes firmly anchored in the lipid bilayer due to the presence of two long alkyl chains and therefore can serve as a fluorescent label. The liposomes thus labeled are bound to a series of prostheses precoated with an amphiphilic agent, as described in Example 9, Step (c), and then is washed with water. The prosthesis test parts are 1–2 cm sections of vascular graft (diameter about 0.5 cm) made of expanded polytetrafluloroethylene sold as Gore-Tex. The prostheses are immersed in 2-ml aliquots of blood plasma for various lengths of time ranging from a few minutes to several hours. One prothesis serving as blank is not treated with plasma. The prostheses are withdrawn and dried. All prostheses are then extracted with 2-ml aliquots of chloroform which dissolves all phospholipid, dye, and amphiphilic agent bound to the prostheses. The fluorescence of each extract is measured on a fluorescense spectrophotometer. An excitation wavelength of 490 nm and an emission wavelength of 520 nm are used. These wavelengths may vary somewhat depending on the composition of the sample. The fraction of dye, and hence of phospholipid, retained after various times of exposure to plasma, is obtained by comparing each reading with the reference blank.

The efficiency of the liposome-binding process is obtained by comparing the fluoresence of the above reference blank with the fluorescense of a solution of 20 mg PS and 0.1 mg DCY in 2 ml of chloroform, which represents the total dye and lipid present initially.

The above tests measure the efficiency of initial binding, and of subsequent retention during exposure to plasma not only of phospholipid but also of an amphiphilic antibiotic encapsulated by liposomes, as in Example 7, since the amphiphilic dye DCY has the same retention characteristics, due to its molecular structure, as an amphiphilic antibiotic.

Tests for Retention of Liposome-enclosed Water-soluble Antibiotic on Prostheses

A. Twenty mg of PS or other lipid are evaporated to dryness from chloroform/methanol solution as in Example 1. To the dried lipid film is added 2 ml of aqueous buffer solution (5 millimolar TRIS or other buffer at pH 7.5) containing the water-soluble fluorescent dye carboxyfluorescein (CF) at a concentration of 1.0 micromolar. The lipid is dispersed by using a vortex mixer and lipid-buffer mixture is then sonicated to form liposomes, as in Example 1. The liposomes are bound to a series of prosthesis parts treated with an amphiphilic agent, as in Example 9, Step (c). The prosthesis test parts are as described in the above test. A number of prosthesis parts so treated are immersed in 2-ml aliquots of blood plasma for various lengths of time, then withdrawn. The plasma samples which now contain any CF detached from the prostheses. The fluorescence of the plasma samples is measured using an excitation wavelength of 470 nm and an emission wavelength of 520 nm. The readings represent the amount of CF that became detached from the polymer either within an intact liposome or as free CF that had leaked out. These amounts are representative of the amount of a water-soluble antibiotic lost during exposure to plasma.

B. Liposomes are prepared containing entrapped CF, as in Example 13, except that now the CF concentration is 200 millimolar. In this highly concentrated state, the dye is non-fluorescent due to self-quenching. The liposomes are bound to a number of prostheses precoated with an amphiphilic agent, as in Example 9, Step (c). Following this step, the prostheses are thoroughly rinsed with an aqueous buffer solution (5 millimolar TRIS or other buffer at pH 7.5) to remove completely any external dye. The prostheses are then immersed in 2-ml aliquots of blood plasma for various lengths of time and then are withdrawn. The fluorescence of the plasma samples is then measured, again at wavelengths of 470 and 520 nm for excitation and emission, respectively. Any fluorescence observed now represents only that amount of dye that has leaked out from the interior of liposomes and had become fluorescent by dilution. Any CF present in intact liposomes that had become detached from the polymer remains non-fluorescent and is not recorded.

The amounts of dye recorded by this method are representative of the amounts of a water-soluble antibiotic lost by leakage from liposomes during exposure to plasma.

The amount of amphiphilic agent or liposomes can be determined by striping the prosthesis with chloroform or other effective solvent. Stability of the liposomes on the surfaces of a prosthesis or implant after freezing and thawing or dehydration, can be determined by measuring the amount and rate of pharmaceuticals in the liposomes appearing in a blood serum bath or other liquid bath surrounding a prosthesis or implant.

The following Examples are in illustration of the invention and are not intended to be limiting.

Abbreviations used in the Examples have the following meanings:

EPC: egg phosphatidyl choline (lecithin)
PS: phosphatidylserine from beef brain
TRIS: tris(hydroxymethyl) aminomethane
TES: N-tris(hydroxymethyl)-methyl-2-aminoethane-sulfonic acid
HEPES: N-2-hydroxyethylpiperazine-N-2-ethane-sulfonic acid
TRIS, TES, and HEPES are well-known biological buffers also known as Good buffers (after the inventor, N. E. Good)
DYC: dioctadecyloxacarbolyamine
CF: carboxyfluorescein
TDMAC: tridodecylmethylammonium chloride

EXAMPLE 1

Preparation of Stabilized Liposomes Containing an Encapsulated Antibiotic

An amount of 20 mg phosphatidyl serine is dissolved in 2 ml chloroform/methanol (2:1 by volume). This solution is placed into a 50-ml round bottom flask and evaporated to dryness in a rotary evaporator under vacuum provided by a water aspirator. The resulting thin film of lipid deposited on the wall of the flask is freed of residual solvent traces by placing it under high vacuum provided by a mechanical pump for one hour. Two ml aqueous 5 millimolar Tris buffer solution at pH 7.5, and containing 10 mg per ml of penicillin G sodium (benzylpenicillin sodium) and 50 mg per ml of sucrose are added to the flask containing the dried lipid film. The flask and contents are agitated for about one minute on a Vortex mixer to detach the lipid from the glass wall and suspending it in the solution which at this point is milky in appearance. The resulting suspension is transferred to a test tube, about 15 mm diameter and 80 mm long, with a rounded or conical end, and is sonicated with a probe-type sonicator fitted with a microtip (Branson Model 140 W, Heat Systems-Ultrasonics Inc.) at 30 watts, for about 45 minutes. During sonication the tube is surrounded by a water bath to maintain the temperature between 25° and 30° C. At the end of the sonication step the solution is almost clear and slightly opalescent. It now contains liposomes of about 30 to 50 nanometers in size, which are mostly unilamellar. The penicillin and sucrose are now present both in the inner compartments of the liposomes and in the external solution. The liposomes are freeze-thaw and dehydration stable.

EXAMPLE 2

The procedure of Example 1 is repeated using the following compositions to provide negatively charged liposomes:

(a) 15 mg egg phosphatidyl choline (EPC)+5 mg phosphatidyl serine (PS).

(b) 15 mg PS+5 mg cholesterol.

(c) 10 mg EPC+5 mg PS+5 mg cholesterol.

(d) 15 mg EPC+5 mg phosphatidic acid.

(e) 15 mg EPC+5 mg dicetyl phosphate.

Other lipid mixtures are possible. The guiding principle is that not less than about 25% of the lipid bear a negative charge. The remainder can be neutral (as is EPC). Addition of cholesterol is optional, as a stiffening agent.

The procedure of Example 1 is also repeated by replacing the natural products EPC and PS (derived from beef brain) in compositions (a)–(e) by phospholipids having defined alkyl chains, such as dimyristoyl, dipalmitoyl, or distearoyl phosphatidyl choline, phosphatidyl serine, and phosphatidyl inositol. Components such as phosphatidic acid, dicetyl phosphate and cholesterol are not used to form vesicles by themselves but are used in conjunction with the above-named phospholipids. The negatively charged liposomes are subsequently bound to prostheses treated with a cationic amphiphilic agent by contacting the prostheses with aqueous dispersions of the liposomes.

EXAMPLE 3

The procedure of Example 1 is repeated for the production of positively charged liposomes using the following lipid compositions:

(a) 15 mg EPC+5 mg stearylamine.

(b) 20 mg tridodecylmethylammonium chloride (TDMAC).

The resulting positively charged liposomes are subsequently bound to prostheses impregnated with an anionic amphiphilic agent.

EXAMPLE 4

Example 1 is repeated using the following buffers instead of the Tris buffer:

(a) 5 millimolar TES, pH 7.5

(b) 5 millimolar HEPES, pH 7.5

EXAMPLE 5

Example 1 is repeated using a bath-type sonicator (Laboratory Supplies Co., 80 kHz, 80 watt) instead of the probe-type sonicator. The test tube containing the sample is stoppered and partly immersed in the sonicator bath. Sonication for 60 to 90 minutes is required to obtain nearclarity. As needed, the temperature is controlled by circulating water through a cooling coil immersed in the bath.

EXAMPLE 6

Example 1 is repeated using the following instead of the sucrose used in Example 1:

(a) 50 mg/ml of trehalose (b) 50 mg/ml of glucose.

EXAMPLE 7

The following illustrates encapsulation of amphiphilic or lipid-soluble antibiotics, as alternative to the encapsulation of water-soluble antibiotics as in Example 1:

Twenty mg of PS (or other lipid or lipid mixture as per Example 2) are dissolved in 2 ml of methanol or chloroform/methanol (2:1), together with 20 mg of an amphiphilic antibiotic. Example of this type of compound include free penicillin G (benzylpenicillinic acid); amphotericin B and other members of the large class of polyene macrolide antibiotics. The solution is evaporated to dryness on a rotary evaporator under vacuum supplied by a water aspirator, then freed of residual solvent under high vacuum. Two ml of an aqueous buffer solution, 5 millimolar in TRIS or other buffer, at pH 7.5, are added. The rest of the procedure is as in Example 1. The resulting liposomes now contain the antibiotic embedded in their lipid bilayer shells, with the lipid moiety of the antibiotic in the bilayer interior, and the polar groups of the antibiotic located in the polar interface of the bilayer. This procedure has the great advantage over Example 1 in that essentially all the antibiotic becomes incorporated in the liposomes. The liposomes are freeze-thaw and dehydration stable.

EXAMPLE 8

The following illustrates recovery of unencapsulated antibiotic: If desired, the liposomes prepared according to Example 1 or its variants are passed through a gel chromatographic column. Suitable column dimensions for the amounts of materials in Example 1 are 4 cm diameter×50 cm long. The packing material is Sephadex G-75® or some other, equivalent medium. With such a column the fractions containing the liposomes with encapsulated antibiotic elute near the void volume and are well separated from the much later fractions containing the antibiotic in the external solution. These latter fractions can be used to suspend and sonicate a further quantity of lipid, thus utilizing the expensive antibiotic more efficiently.

EXAMPLE 9

Preparation of Prostheses Carrying Liposome-encapsulated Antibiotic

Step (a): A length of 1–2 cm of vascular graft prosthesis made of expanded PTFE (Goretex®) is immersed in 2 ml of a 0.5% solution of TDMAC in methanol for one hour, then withdrawn and dried. By this procedure, TDMAC, a cationic amphiphilic agent, is bound to the polymer.

Step (b): The vascular graft prosthesis which has amphiphilic agent bound to it is immersed in 2 ml of suspension of Sepharose-CM. This product is an aqueous suspension of microscopic beads of a crosslinked polysaccharide carrying carboxymethyl groups. The beads have a diameter of 40–260 microns in the swollen state. This material strips off TDMAC from the exposed exterior surfaces of the prosthesis but leaves in place TDMAC located on the surfaces of crevices and inner passages which the Sepharose-CM beads do not contact. The purpose of this step (which may be omitted without affecting the remainder of this procedure) is to reduce or eliminate thrombogenic effects due to TDMAC on exposed polymer surfaces.

Step (c): The graft prosthesis, now carrying TDMAC on its inner surfaces, is immersed for 12 hours in 2 ml of an aqueous suspension of negatively charged liposomes carrying an antibiotic encapsulated either in their inner aqueous compartments or within their bilayer shells. This suspension contains 10 mg/ml of lipid, 50 mg/ml of sucrose or other saccharide, and an amount of antibiotic, depending on the method of preparation, of 10 mg/ml or less which may be fully or partly encapsulated. The graft may be withdrawn at the end of the immersion period, rinsed in water, and used immediately.

Step (d): If the graft prosthesis is to be stored for future use, it is left in the liposome suspension which is then packaged and sealed in a plastic pouch kit. The kit is stored in a freezer at $-20°$ C. or colder. In this state, the polymer—liposome—antibiotic system has long-term stability. When required for use, the kit is allowed to thaw, and the graft prosthesis is rinsed in water.

The order of above steps (b) and (c) can be reversed. This provides a graft prosthesis with some liposomes also on the outer surfaces of the prosthesis but the treatment with Sepharose-CM removes TDMAC not bound to liposomes.

All of the foregoing steps are performed under aseptic conditions.

EXAMPLE 10

In place of TDMAC, as in Example 9, Step (a) the polymer is treated with an anionic amphiphilic agent, again 0.5% in methanol. Amphiphilic agents used include PS, phosphatidic acid, and phosphatidyl glycerol. A suspension of positively charged liposomes is used in Step (c).

EXAMPLE 11

Alternative long-term storage conditions:

After Step (c) in Example 9, the graft prosthesis is withdrawn from the liposome suspension. It is placed into an empty flask which is then immersed in a freezing bath consisting of dry ice/methanol, or liquid nitrogen, long enough to freeze the aqueous suspension on and within the polymer. The sample then is freeze-dried in a freeze dryer by applying vacuum for 12-15 hours. The resulting graft prosthesis now has a relatively large amount of dry sucrose and a small amount of dried lipsomes on its surfaces. In this state, it can be packaged and sealed in a kit (again under aseptic conditions) and stored at room temperature ona long-term basis. When required for use, the graft prosthesis is rehydrated by suspending it in sterile water. Rehydration is almost instantaneous, but is continued for about 10 minutes to ensure complete rehydration.

What is claimed is:

1. A sterile prosthesis or implant which is adapted for use in in vivo surgery having bound to the surfaces thereof liposomes, and bound to said liposomes at least one saccharide stabilizing agent in which liposomes are enveloped at least one pharmaceutical agent acceptable to the body tissues and fluids surrounding said prosthesis or implant and which can be prepared outside the operating room and stored under sterile conditions prior to use in surgery, said liposomes being stable to freezing and thawing or drying and being capable of rapid reconstitution at the time required for surgery, said prosthesis or implant resisting the development of infection or thrombosis in its in vivo environment.

2. A prosthesis or implant of claim 1, the surface of which is treated with an amphiphilic agent prior to binding of said liposomes to said surface, said amphiphilic agent being biocompatible and being capable of binding said liposomes having opposite charge to the charge of said amphiphilic agent.

3. A prosthesis or implant of claim 2, wherein the amount of said amphiphilic agent bound to the surface of the prosthesis or implant is present in an amount required for binding said liposomes but not in substantial excess of said amount.

4. A prosthesis or implant of claim 2, wherein the prosthesis or implant is free of any substantial excess of the amphiphilic agent from the outer surface of the prosthesis or implant over that amount of amphiphilic agent required to bind said liposomes, prior to the binding of said liposomes.

5. A prosthesis or implant of claim 2, wherein said amphiphilic agent is cationic.

6. A prosthesis or implant of claim 5, wherein said amphiphilic agent is TDMAC.

7. A prosthesis or implant of claim 5, wherein the amount of said amphiphilic agent bound to the surface of the prosthesis or implant is present in an amount required for binding said liposomes but not in substantial excess of said amount.

8. A prosthesis or implant of claim 2, wherein said amphiphilic agent is anionic.

9. The prosthesis or implant of claim 1, wherein said saccharide stabilizing agent is selected from the group consisting of a monosaccharide, di-saccharide and glycoside thereof having a lipophilic moiety said prosthesis or implant rendered stable to freeze-thawing by preparing the liposomes in the presence of about 5% to about 10% solution of said saccharide agent to avoid loss of encapsulated antibiotic and aggregation and fusion of the liposomes.

10. A prosthesis or implant of claim 9 wherein the saccharide is sucrose, trehalose or glucose.

11. A prosthesis or implant of claim 1 wherein a biocompatible antibiotic is enveloped in said liposomes.

12. A prosthesis or implant of claim 1 wherein said bound liposomes are in a frozen state.

13. A prosthesis or implant of claim 1 wherein said bound liposomes are in a dehydrated state.

14. A prosthesis or implant of claim 1 wherein the liposomes are unilamellar having predominantly a diameter less than 100 nanometers.

15. The prosthesis or implant of claim 1 which has structural means for use and is adapted for a use selected from the group consisting of vascular, heart valve, orthopedic, ventricular, peritoneovenous shunt, penile, intraocular or catheter prosthesis.

16. A prosthesis of claim 1 which is made of porous polytetrafluoroethylene.

17. A prosthesis of claim 1 which is made of poly (ethylene-p-phthalate).

18. A kit comprising a sealed and sterile package containing a sterile prosthesis or implant which is adapted for use in vivo surgery having bound to the surfaces thereof liposomes, and bound to said liposomes at least one saccharide stabilization agent in which liposomes are enveloped at least one pharmaceutical agent acceptable to the body tissues and fluids surrounding said prosthesis or implant and which can be prepared outside the operating room and stored under sterile conditions prior to use in surgery, said liposomes being stable to freezing and thawing or drying due to the presence of at least one saccharide and being capable of rapid reconstitution at the time required for surgery, said prosthesis or implant resisting the development of infection or thrombosis in its in vivo environment.

19. A kit of claim 16 wherein the liposomes of contained prosthesis or implant of claim 1 are in a frozen state.

20. A kit of claim 18 wherein the liposomes of contained prosthesis or implant are in a dehydrated state.

21. The kit according to claim 18 wherein the saccharide is selected from the group consisting of a monosaccharide, disaccharide and glycoside thereof having a lipophilic moiety.

22. The kit according to claim 21 wherein the saccharide is selected from the group consisting of sucrose, trehalose and glucose.

* * * * *